United States Patent [19]

Freenor, III et al.

[11] 4,125,397
[45] Nov. 14, 1978

[54] O-SULFONYL-ALPHA-HALO-2,6-DIHALOBENZALDOXIMES

[75] Inventors: Francis J. Freenor, III, Richmond; Barbara M. Koerber, Berkeley, both of Calif.

[73] Assignee: Chevron Research Company, San Francisco, Calif.

[21] Appl. No.: 756,567

[22] Filed: Jan. 3, 1977

[51] Int. Cl.$^2$ .............................................. A01N 9/14
[52] U.S. Cl. ................................... 71/103; 260/543 R
[58] Field of Search .............. 71/103, 121; 260/543 R

[56] References Cited

U.S. PATENT DOCUMENTS

| 3,165,392 | 1/1965 | Koopman | 71/106 |
| 3,234,255 | 2/1966 | Hackmann et al. | 71/103 |
| 3,717,690 | 2/1973 | Newman | 71/103 |
| 3,752,661 | 8/1973 | Orlett | 71/103 |
| 3,896,155 | 7/1975 | Hamprecht et al. | 71/103 |

Primary Examiner—Glennon H. Hollrah
Attorney, Agent, or Firm—Dix A. Newell; T. G. DeJonghe; Raymond Owyang

[57] ABSTRACT

O-alkylsulfonyl- and O-haloalkylsulfonyl-alpha-halo-2,6-dihalobenzaldoximes are active pre-emergent herbicides.

16 Claims, No Drawings

O-SULFONYL-ALPHA-HALO-2,6-DIHALOBENZALDOXIMES

BACKGROUND OF THE INVENTION

U.S. Pat. Nos. 3,165,392; 3,223,733; 3,234,255; 3,483,246; 3,495,968; 3,549,702 and 3,575,972 disclose pesticidal benzaldoximes, e.g., alpha-cyano-2,6-dichlorobenzaldoxime and alpha,2,6-trichlorobenzaldoxime.

DESCRIPTION OF THE INVENTION

The herbicidal benzaldoximes of the invention are represented by the formula (I)

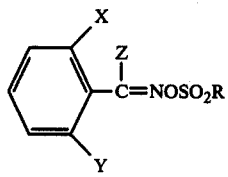

wherein R is alkyl of 1 to 6 carbon atoms or haloalkyl of 1 to 6 carbon atoms and of 1 to 5 fluoro, chloro, bromo or iodo; Z is chloro or bromo; X is chloro or bromo and Y is chloro or bromo.

Representative alkyl R groups include methyl, ethyl, propyl, sec-butyl, etc. Representative haloalkyl R groups include fluoromethyl, chloromethyl, iodomethyl, dibromomethyl, trichloromethyl, 2-chloroethyl, pentachloroethyl, 2,2,2-trichloroethyl, 3-chloropropyl, 4-bromobutyl, etc.

Preferably R is alkyl of 1 to 3 carbon atoms or haloalkyl of 1 to 3 carbon atoms and 1 to 3 fluoro, chloro or bromo groups. Most preferably R is chloroalkyl of 1 to 3 carbon atoms and 1 to 3 chloro groups. Preferably X, Y and Z are chloro.

Representative benzaldoxime esters of the invention are:
O-methylsulfonyl-alpha-chloro-2,6-dichlorobenzaldoxime,
O-isopropylsulfonyl-alpha-chloro-2-chloro-6-bromobenzaldoxime,
O-fluoromethylsulfonyl-alpha-bromo-2,6-dichlorobenzaldoxime,
O-dichloromethylsulfonyl-alpha-bromo-2,6-dichlorobenzaldoxime,
O-(2-bromoethylsulfonyl)-alpha-bromo-2-chloro-6-bromobenzaldoxime, and
O-(1,1,2,2-tetrachloroethylsulfonyl)-alpha-bromo-2,6-dibromobenzaldoxime.

The alpha-halobenzaldoximes of the invention can exist as syn- or anti-isomers or as mixtures thereof and the present invention relates to any or all of these forms.

The compounds of the invention are prepared by reacting an alpha-halo-2,6-dihalobenzaldoxime with a sulfonyl chloride compound of the formula $RSO_2Cl$ wherein R has the same significance as previously defined. Generally, the reaction is conducted by reacting substantially equimolar amounts of the alpha-halo-2,6-dihalobenzaldoxime and the sulfonyl chloride in an inert diluent at a temperature of 0° to 100° C. When alpha-halo-2,6-dihalobenzaldoxime is employed as the reactant, it is generally convenient to employ an acid acceptor. Suitable acid acceptors are organic amines such as pyridene compounds, e.g., pyridine or alphapicoline, and lower trialkylamines, e.g., triethylamine or tripropylamine, and alkali metal carbonates, e.g., sodium carbonate. Generally, at least one mol of acid acceptor is employed for each mol of sulfonyl chloride.

The product (I) is isolated and purified by conventional procedures such as extraction, filtration, crystallization and chromatography. The product (I) is generally a mixture of the syn- and anti-isomers. However, the pure anti- or syn-isomers can be obtained by crystallization or chromatography.

EXAMPLES

Example 1 -- Preparation of O-isopropylsulfonyl-alpha-chloro-2,6-dichlorobenzaldoxime A 3.6 (0.036 mol) sample of triethylamine was added slowly to a cooled mixture (ice bath) of 7.8 g (0.035 mol) alpha-chloro-2,6-dichlorobenzaldoxime (U.S. Pat. No. 3,234,255) and 5.5 g (0.035 mol) isopropylsulfonyl chloride in 125 ml diethyl ether. The reaction was slightly exothermic. The reaction mixture was filtered to remove a small amount of salts and the filtrate was evaporated under reduced pressure to give a yellow oil. The oil was chromatographed through a silica gel column with hexane/dichloromethane elution. O-isopropylsulfonyl-alpha-chloro-2,6-dichlorobenzaldoxime (white solid, m.p. 48°–50° C.) was eluted from the column with dichloromethane. Elemental analysis for $C_{11}H_{12}Cl_3NO_3S$ showed: %S, calc. 9.3, found 8.1; %Cl, calc. 30.9, found 32.8.

Example 2 -- Preparation of O-(3-chloropropylsulfonyl)-alpha-chloro-2,6-dichlorobenzaldoxime A 3.6 g (0.034 mol) sample of 2,6-dimethylpyridine was added dropwise to a cooled solution (ice bath) of 7.4 g (0.033 mol) alpha-chloro-2,6-dichlorobenzaldoxime and 5.9 g (0.03 mol) 3-chloropropylsulfonyl chloride in 75 ml benzene. The reaction mixture was allowed to warm to 25° C., stirred for 2 hours (a red solid formed) and allowed to stand overnight. The reaction mixture was evaporated under reduced pressure and the residue was chromatographed through a silica gel column with dichloromethane. A semi-crystalline yellow product was eluted from the column. The product was recrystallized from ether/hexane to give 4.3 g of O-(3-chloropropyl)-alpha-chloro-2,6-dichlorobenzaldoxime as a white solid, m.p. 69°–71° C. Elemental analysis for $C_{10}H_9Cl_4NO_3S$ showed: %S, calc. 8.8, found 9.2; %Cl, calc. 38.8, found 37.9.

Example 3 -- Preparation of O-methylsulfonyl-alpha-chloro-2,6-dichlorobenzaldoxime This product was prepared by a procedure similar to that of Examples 1–2. The product is a white solid melting at 117° C. Elemental analysis for $C_8H_6Cl_3$S showed: %S, calc. 10.6, found 10.4; %Cl, calc. 35.2, found 31.2.

Example 4 -- Preparation of O-ethylsulfonyl-alpha-chloro-2,6-dichlorobenzaldoxime This product was prepared by a procedure similar to that of Example 2. The product is a white solid, melting at 89–92° C. Elemental analysis for $C_9H_8Cl_3NO_3S$ showed: %S, calc. 10.1, found 10.3; %Cl, calc. 33.6, found 32.8.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are most effective when applied pre-emergently.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 mcg/cm$^2$. The pot was watered and placed in a greenhouse. The pot was watered intermittently and was observed for seedling emergence, health and emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

TABLE I

| Example | O | W | C | M | P | L |
|---|---|---|---|---|---|---|
| 1 | 0 | 0 | 0 | 45 | 100 | 100 |
| 2 | 100 | 35 | 35 | 100 | 100 | 100 |
| 3 | 95 | 45 | 50 | 85 | 85 | 100 |
| 4 | 10 | 0 | 0 | 20 | 100 | 100 |

O = Wild Oats (*Avena fatua*)
W = Watergrass (*Echlinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:

1. A compound of the formula

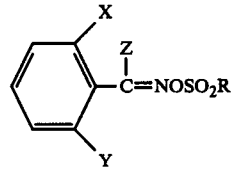

wherein R is alkyl of 1 to 6 carbon atoms or chloroalkyl of 1 to 3 carbon atoms and of 1 to 3 chloro groups, Z is chloro or bromo, X is chloro or bromo and Y is chloro or bromo.

2. The compound of claim 1 wherein R is alkyl and Z is chloro.

3. The compound of claim 1 wherein R is methyl, and X, Y and Z are chloro.

4. The compound of claim 1 wherein R is chloroalkyl of 1 to 3 carbon atoms and of 1 to 3 chloro groups.

5. The compound of claim 1 wherein R is 3-chloropropyl and X, Y and Z are chloro.

6. A method for the pre-emergent control of undesirable vegetation which comprises applying to the growth medium of the vegetation a herbicidally effective amount of the compound defined in claim 1.

7. The method of claim 6 wherein R is alkyl.

8. The method of claim 6 wherein R is methyl, and X, Y and Z are chloro.

9. The method of claim 6 wherein R is chloroalkyl of 1 to 3 carbon atoms and 1 to 3 chloro groups.

10. The method of claim 6 wherein R is 3-chloropropyl and X, Y and Z are chloro.

11. The method of claim 6 wherein the compound is applied pre-emergently to mustard, pigweed or lambsquarter.

12. A herbicidal composition comprising a biologically inert carrier and a herbicidally effective amount of the compound of claim 1.

13. The composition of claim 12 wherein R is alkyl.

14. The composition of claim 12 wherein R is methyl, and X, Y and Z are chloro.

15. The method of claim 12 wherein R is chloroalkyl of 1 to 3 carbon atoms and 1 to 3 chloro groups.

16. The composition of claim 12 wherein R is 3-chloropropyl and X, Y and Z are chloro.